(12) United States Patent
Foster

(10) Patent No.: US 9,162,018 B2
(45) Date of Patent: Oct. 20, 2015

(54) CARDIAC PUMP

(75) Inventor: Graham Foster, Swansea (GB)

(73) Assignee: Calon Cardio Technology Limited, Swansea (GB)

(*) Notice: Subject to any disclaimer, the term of this patent is extended or adjusted under 35 U.S.C. 154(b) by 0 days.

(21) Appl. No.: 14/233,703

(22) PCT Filed: Jul. 18, 2012

(86) PCT No.: PCT/GB2012/051714
§ 371 (c)(1),
(2), (4) Date: Jan. 17, 2014

(87) PCT Pub. No.: WO2013/011308
PCT Pub. Date: Jan. 24, 2013

(65) Prior Publication Data
US 2014/0155683 A1   Jun. 5, 2014

(30) Foreign Application Priority Data
Jul. 18, 2011   (GB) .................................. 1112350.2

(51) Int. Cl.
*A61M 1/10* (2006.01)
*A61M 1/12* (2006.01)

(52) U.S. Cl.
CPC .............. *A61M 1/101* (2013.01); *A61M 1/1031* (2014.02); *A61M 1/122* (2014.02)

(58) Field of Classification Search
CPC ....... A61M 1/10; A61M 1/101; A61M 1/122; A61M 1/1012; A61M 1/1031
USPC ................... 600/16; 623/3.1, 3.11, 3.13, 3.15
See application file for complete search history.

(56) References Cited

U.S. PATENT DOCUMENTS

| 4,704,121 | A | 11/1987 | Moise |
| 5,399,074 | A * | 3/1995 | Nose et al. ................. 417/423.1 |
| 5,588,812 | A | 12/1996 | Taylor et al. |
| 5,613,935 | A | 3/1997 | Jarvick |
| 7,416,525 | B2 * | 8/2008 | Wampler et al. ................ 600/16 |
| 2003/0113208 | A1 * | 6/2003 | Hart et al. ..................... 415/206 |
| 2007/0249888 | A1 * | 10/2007 | Wu et al. ........................ 600/16 |
| 2011/0238172 | A1 | 9/2011 | Akdis |

* cited by examiner

*Primary Examiner* — Joseph Dietrich
(74) *Attorney, Agent, or Firm* — Larson & Anderson, LLC

(57) ABSTRACT

The cardiac pump, which is suitable for implantation into a ventricle of a human heart, has a primary blood flow path through a housing, a rotatable pump member disposed within the housing for causing blood to flow along the primary flow path, the pump member being rotatably coupled to the housing about an upstream bearing and a downstream bearing. The pump member includes an impeller shroud defining a secondary flow path in fluid communication with the primary flow path. The downstream bearing comprises a rotational bearing member and a stationary bearing seat for the bearing member, there being a circumferential transition between the bearing seat and the bearing member, the circumferential transition being disposed in the secondary flow path and arranged to be washed by blood passing along the secondary flow path.

9 Claims, 5 Drawing Sheets

CARDIAC PUMP

The present invention concerns miniaturised pumps suitable for implantation into the human heart or vascular system.

Heart Failure is major global health problem resulting in many thousands of deaths each year. Until recently the only way to curatively treat advanced heart failure has been by heart transplant or the implantation of a total mechanical heart. Unfortunately donor hearts are only able to meet a tiny fraction of the demand and total mechanical hearts have yet to gain widespread acceptance due to the technical difficulties involved with these devices.

Ventricular assist devices (VADs) have been gaining increased acceptance over the last decade primarily as a bridge to transplant devices. The devices are implanted long term and work alongside a diseased heart to boost its output and keep the patient alive and/or give a better quality of life whilst awaiting transplant.

The use of these devices has shown that it most cases once the device has been implanted the heart failure does not progress any further and the patient recovers a good quality of life. In cases where a heart transplant has not been available patients have lived for several years with an VAD fitted without major complications.

Therefore a VAD can be considered a viable alternative to heart transplantion and offers hope to the many thousands of heart failure patients for whom a donor heart will not be available.

At present, the main reasons preventing VADs from being fitted on a more routine basis is the invasive surgical procedure required to fit the devices, and the high cost of the devices themselves.

With regard to the surgery, typically a sternotomy, full heart lung bypass, and major procedures to the heart, thoracic aorta and abdominal cavity are required to fit a VAD. Presently the risk of such an operation cannot be justified except in the case of those in the most advanced stages of Heart Failure.

With regard to cost, current devices are typically of complex construction and require specialised and expensive manufacturing processes for their construction. The surgery required to fit them is also expensive due to being a long and intensive operation.

If the long term implantation of a VAD or an equivalent circulatory assist device could be achieved with a less invasive surgical procedure, certainly eliminating any procedures to the abdominal cavity and ideally eliminating the need for a sternotomy and heart lung bypass, and the cost of the devices could be significantly reduced then the use of VADs to treat heart failure could become far more widespread and routine.

The key to a less invasive implantation procedure for a VAD is to make the device as small as possible so that it can be implanted entirely within the pericardial space eliminating the need for any procedures to abdominal cavity. Furthermore, a device small enough to be implanted via a thoracotomy as opposed to a full sternotomy would be beneficial for those cases where this approach is suitable.

It is also important to minimise surgical risks so it is beneficial to use existing proven techniques, improving on them where possible. A well proven method of implanting current VADs is attaching the devices directly to the apex of the left ventricle, with an inlet to the device residing within the ventricle and the outlet of the device sitting outside of the heart. This eliminates the need for a separate inflow cannula reducing the potential for complications. The workings of the pump (impellor, motor, etc) may reside mostly within the ventricle, across the ventricle wall, or mostly outside of the ventricle depending on the design of the device.

An important factor in the design of a VAD is that the passage of blood through the pump must be constant without areas of flow stasis that could be prone to the formation of thrombus. It is particularly important that bearings are well washed with a constant supply of fresh blood as the heat and geometrical constraints in these areas make them potentially prone to thrombus formation.

A non-essential but highly beneficial requirement of a VAD is that its operational efficiency is as high as possible and is achieved by the combination of the motor efficiency and the pump efficiency. High efficiencies provide benefits such as extended battery life, smaller power cables and the possibility for transcutaneous powering of the pump via an implantable inductive coil.

As a result of the above considerations, there exists a need to develop miniaturised cardiac pumps suitable for implantation into the human heart or vascular system. In addition, such miniaturised devices would benefit by adopting known low risk surgical procedures for their fitment. Another requirement is for bearings of the pump to be well washed with blood to minimise the chances of thrombus formation in operation. It is also highly beneficial for the pump to be as efficient as possible. A further requirement is for the pump to be small enough to be implanted entirely within the pericardial space without surgery to the abdominal cavity.

U.S. Pat. No. 5,092,879 (Jarvik) discloses intraventricular artificial hearts which comprise electrically driven pumps to pump the blood around the body. The pumps disclosed in Jarvik comprise impellers which are rotatably coupled to a support hub; a blood flow is provided to the support hub to wash blood over the support hub to maintain a suitable blood flow. However, the blood supply to the support hub is derived from a junction within a blood flow path which causes the blood flow to split into two streams and utilises a complicated double sided impeller and magnetic bearing arrangement to pump the two streams in the same direction toward the pump outlet.

U.S. Pat. No. 5,399,074 (Kyocera) discloses an extracorporeal bypass pump, one embodiment of which includes channels behind the impeller shroud to allow blood to wash behind the shroud and return to the primary blood flow path. However, the channels do not encourage blood to flow over the bearing, leaving the bearings in an area of stagnant blood which is prone to thrombus (clot) formation.

In general terms a cardiac pump suitable for implantation into a ventricle of a human heart, is known which comprises a housing comprising an inlet for blood, an outlet for blood and a primary blood flow path which extends between the inlet and the outlet; and a rotatable pump member disposed within the housing for causing blood to flow along the primary flow path from the inlet to the outlet.

In such known devices, the pump member may be rotatably coupled to the housing about respective upstream and downstream bearings, and may comprise an impeller with an impeller shroud defining a secondary flow path between the pump member and the housing.

According to the invention there is provided a cardiac pump suitable for implantation into a ventricle of a human heart, the pump being as defined in claim 1. Specifically, the downstream bearing comprises a rotational bearing member and a stationary bearing seat for the bearing member, there being a circumferential transition between the bearing seat and the bearing member, the circumferential transition being disposed in the secondary flow path and arranged to be washed by blood passing along the secondary flow path.

Preferred features of the invention are set out in the subsidiary claims and in the following description.

As used herein, the term "downstream" is with reference to the direction of the primary flow in the primary flow path. That is any part which is nearer to the inlet of the housing (that is, closer to the source of blood flow through the pump) is considered to be upstream, and any part (such as the downstream bearing as described) to which the blood flows on its path between the inlet and the outlet is considered to be "downstream".

The pump according to the invention is to be implanted by attachment to the apex of the heart, and can be small enough to be implanted wholly within the pericardial cavity. The positioning of the secondary flow entrance and exit relative to the primary flow path ensures an adequately washed bearing about which the impeller is arranged to rotate.

As indicated in claim 1, the pump member is rotatably coupled to the housing by an upstream bearing and a downstream bearing. Preferably at least the downstream bearing comprises a recess and a complementarily shaped protrusion to seat in the recess, whereby the secondary flow path washes the transition between the recess and the protrusion.

A preferred example of such a bearing is a ball and socket (ball and cup) bearing in which a convex protrusion (the ball) is seated in a complementarily shaped concave socket (the cup).

It is particularly preferred that the downstream bearing has the ball or equivalent protrusion on the rotatable pump member, and the socket in the housing.

On the other hand, it is preferred that the upstream bearing has the socket in the rotatable pump member and the ball or equivalent protrusion in the housing.

The pump preferably has, subject to the constraints of manufacturing tolerances, smooth continuous contours in the surfaces of the rotatable pump member and the housing adjacent the transition between the rotational bearing member and the stationary bearing seat of the downstream bearing, which as indicated is preferably in the form of a ball and socket. The transition between the bearing member and bearing seat is thereby washed by the continual flow of blood in the secondary flow path over these smooth continuous contours.

This washing of the transition between bearing member and bearing seat reduces the likelihood of blood stagnating and resting in and around that zone, because the volume of blood in the pump is constantly urged to move and flow along the secondary flow path located between the impeller and the impeller shroud. The smooth continuous contours adjacent the transition between the bearing member and the bearing seat) also help to avoid discontinuities which could otherwise lead to stagnant zones or turbulence and could then be thrombus-causing.

It is envisaged that the washing action provided would also be present with other types of bearing located in the secondary flow path and around which the impeller is arranged to rotate.

The blood exiting the secondary flow path is preferably arranged to pass back into the primary flow path and the secondary flow path exit is preferably arranged to direct a flow of blood into the primary flow path in a direction which is substantially coincident with a direction of blood flow along the primary flow path adjacent the exit.

The disposition of the secondary flow entrance relative to the secondary flow exit within the primary flow path avoids the need for a junction in the primary flow path for splitting the flow of blood, and the subsequent complexities to the impeller design this introduces.

In a preferred embodiment of the invention, the pump comprises an impeller and outlet that reside outside of the heart, and a combined motor and inlet cannula section that straddles the wall of the ventricle and extends into the ventricle itself.

The motor rotor components may be attached to the impeller and extend into the inlet cannula. The motor stator components may be integrated into the inlet cannula adjacent to the rotor components.

The layout of the pump according to the invention provides significant advantages and allows the earlier discussed considerations to be achieved: positioning the impeller outside of the heart where there is a space available allows a larger diameter of impeller to be used to enhance efficiency. Integrating the motor components into the inlet cannula provides a convenient position for the motor without increasing the overall size of the pump.

Embodiments of the invention and preferred features thereof will now be described in more detail, with reference to accompanying drawings, in which.

Figure 1:
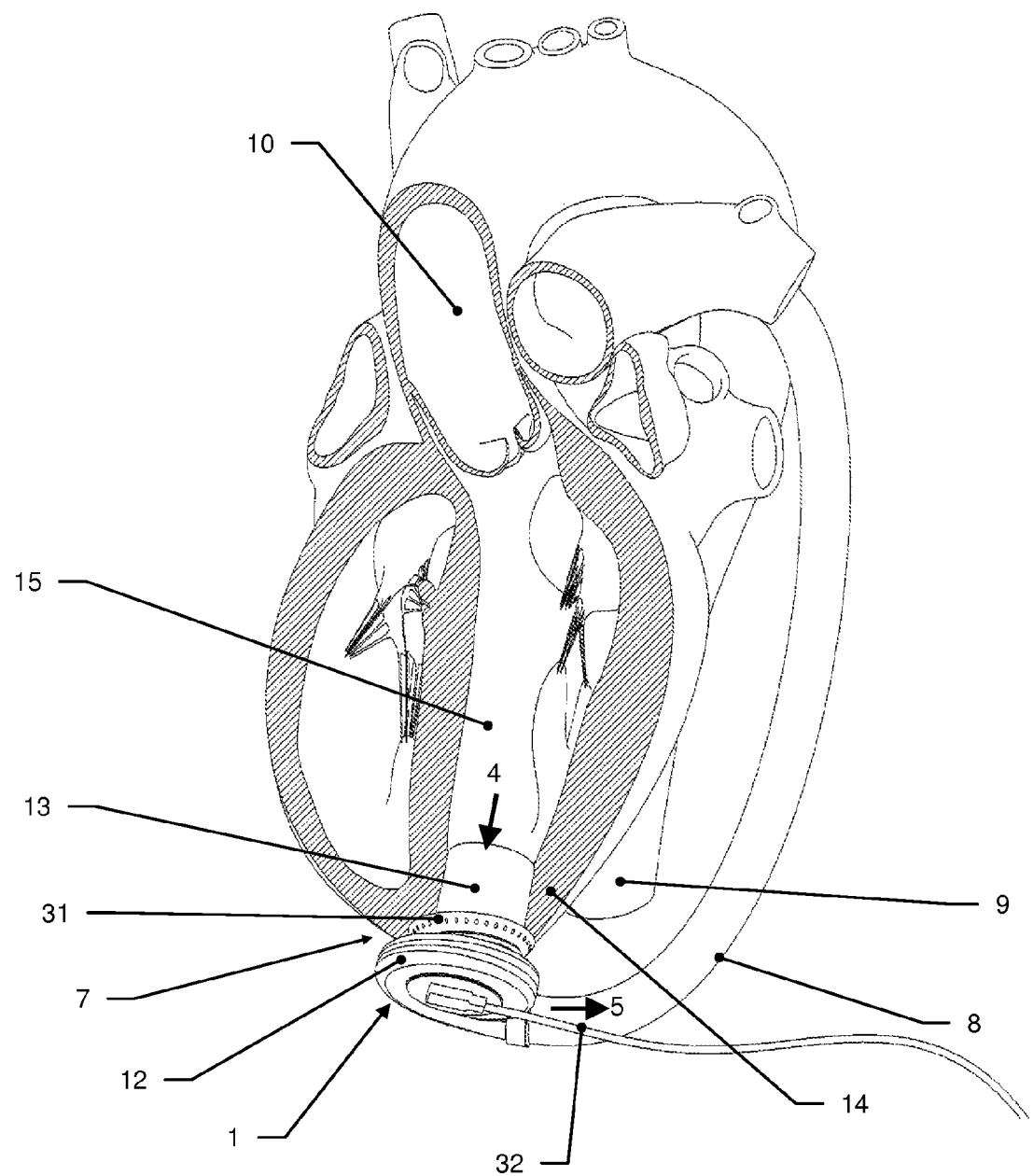
FIG. 1 is a cutaway view of a first embodiment of the pump according to the invention implanted into the human heart.
Figure 2:
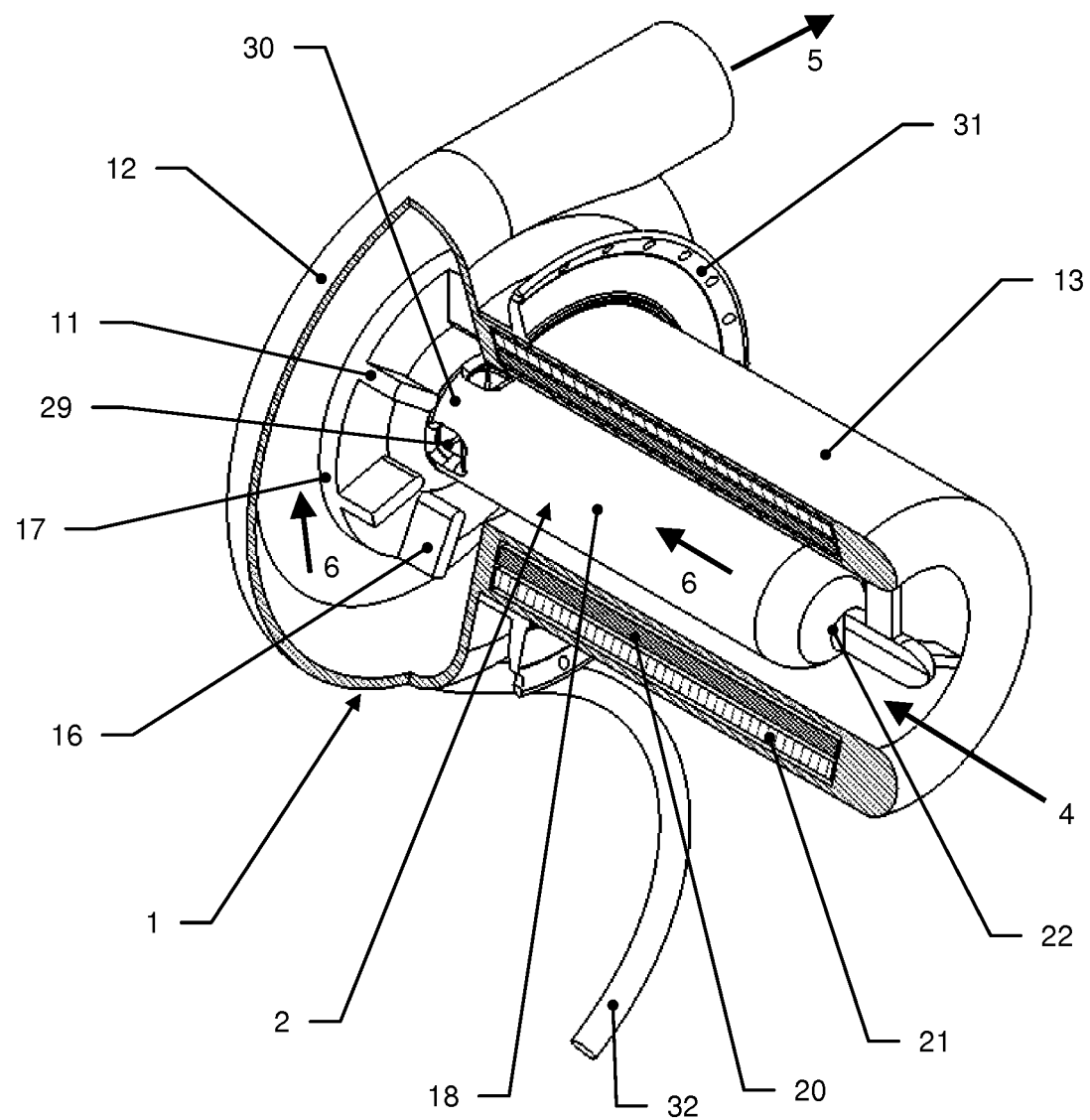
FIG. 2 is a perspective cutaway view of the pump of FIG. 1.
Figure 3:
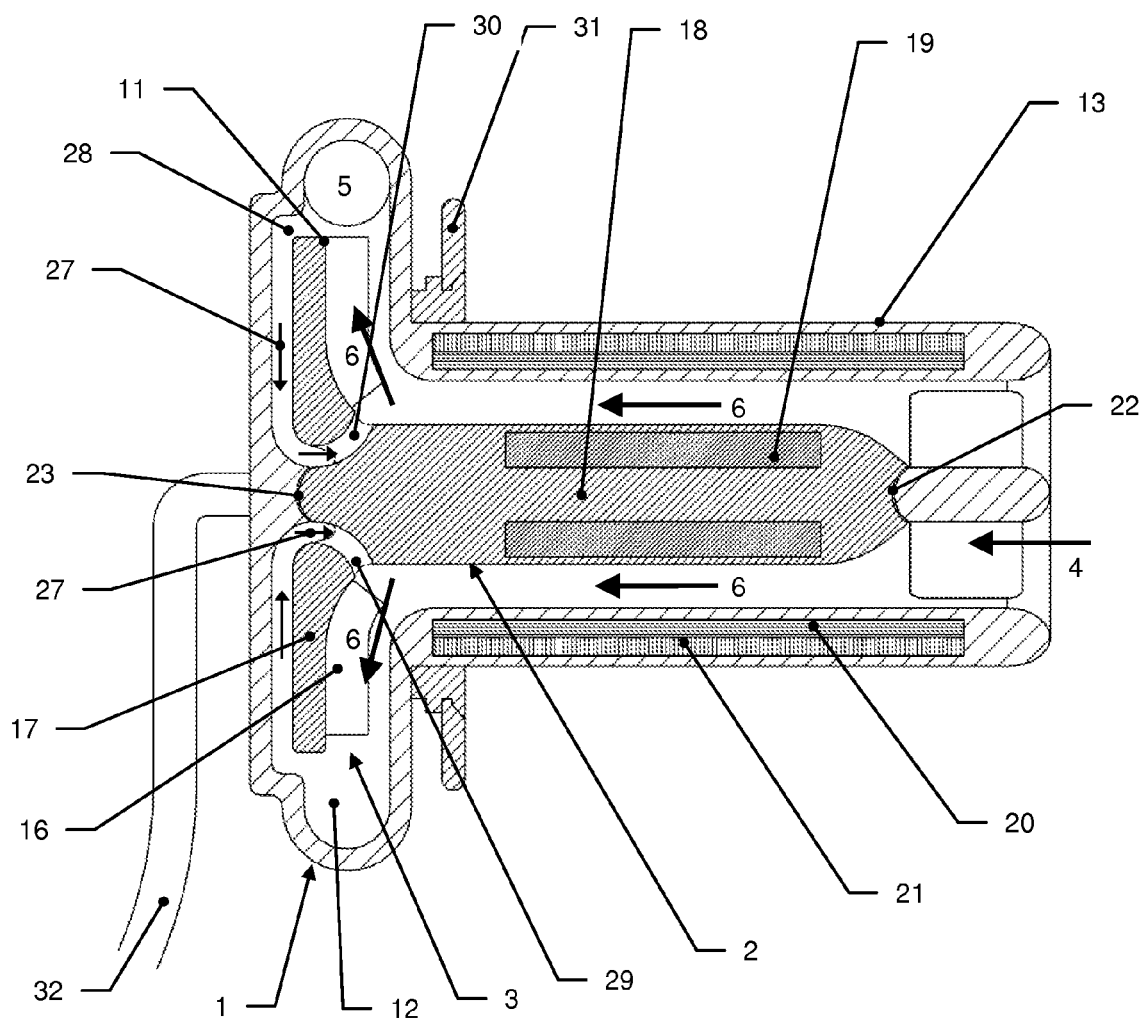
FIG. 3 is a full sectional view of the pump of FIG. 1.

Referring to FIGS. 1 to 3 of the accompanying drawings, in which like parts are denoted by like reference numerals, there is shown a first embodiment of a cardiac pump, comprising an outer casing 1 and single rotating member 2. Defined by the outer casing 1 and the single rotating member 2 is a pumping chamber 3, an inlet 4 for blood, and an outlet 5 for blood. A primary blood flow path 6 is created between the inlet 4 and the outlet 5.

The pumping chamber 3 resides outside of the heart on the apex of the ventricle 7 (FIG. 1) with its outlet 5 connected to an outflow cannula 8 which is in turn grafted to the descending aorta 9. It is also possible to graft the outflow cannula 8 to the ascending aorta 10 (graft not shown).

The positioning of the pumping chamber 3 outside of the heart (for example as shown in FIG. 1) allows the overall pump to be significantly larger than would be possible if it were to be fully implanted into the heart.

As shown in FIG. 1, an inflow cannula 13 extends between the pumping chamber 3, through the wall of the ventricle 14 into the chamber of the ventricle 15, so that the inlet is completely within the chamber of the ventricle 15.

Reverting to FIGS. 2 and 3, the pumping chamber 3 further comprises an impeller 11 that is an integral part of the single rotating member 2. The impeller 11 is preferably of a radial or mixed flow type and is surrounded by a volute 12, which aids the conversion of kinetic energy to pressure energy thus improving efficiency. The impeller 11 comprises a series of impeller blades 16 that are connected by a shroud 17.

As indicated, positioning of the pumping chamber outside the heart enables both the impeller 11 and volute 12 to be of an optimised design to the benefit of both pumping capacity and efficiency.

The motor that powers the pump in the illustrated embodiment of FIGS. 1 to 4 is integrated into the inflow cannula 13. The motor rotor 18 is integral to the single rotating member 2 that also comprises the impeller 11 and extends from the pumping chamber 3 through the length of the inflow cannula 13 to the pump inlet 4, and contains permanent magnets 19. The static motor components of a coil 20 and laminations 21 are incorporated into the wall of the inflow cannula 13.

Figure 4:
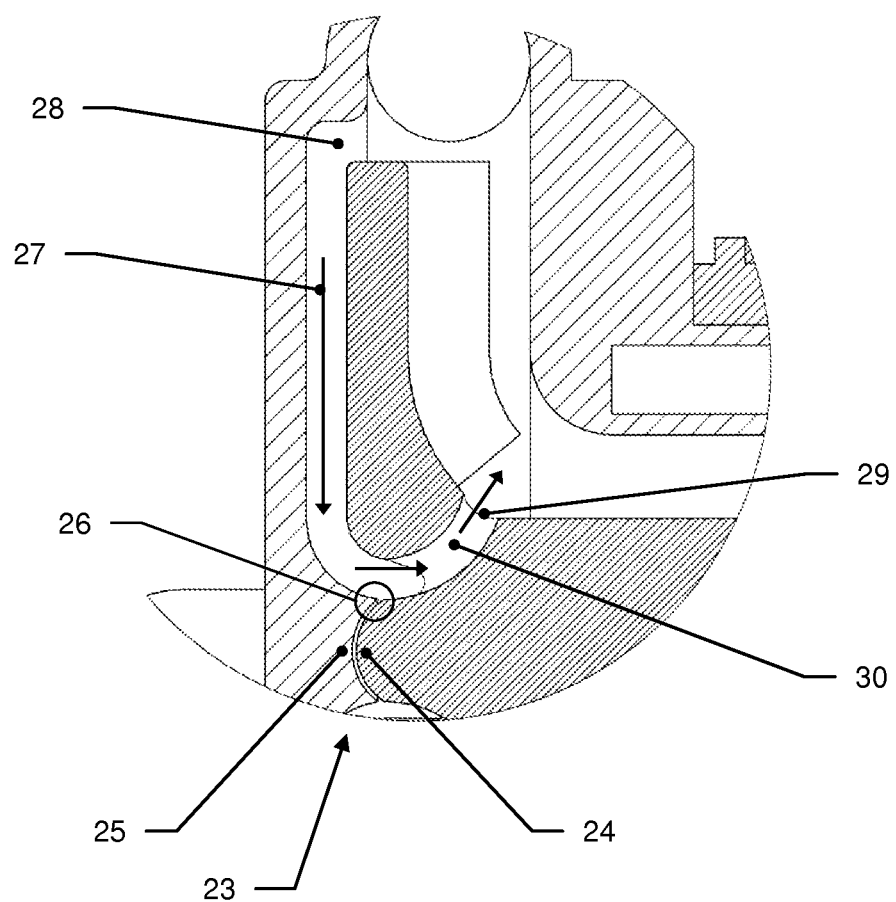
FIG. 4 is an enlarged detail view of FIG. 3.

The single rotating member 2 is rotationally suspended relative to the casing 1 by an upstream bearing 22 at the inlet 4 end of the pump and a downstream bearing 23 at the outlet 5 end of the pump, both the upstream bearing 22 and the downstream bearing 23 being in the form of respective ball 24 and cup 25 members (see FIG. 4 for additional detail of the downstream bearing 23).

It should be noted that the respective ball 24 and cup 25 features can be reversed in orientation, i.e. the ball 24 could be in the stationary casing 1 of the pump instead of the single rotating member 2, whilst the cup 25 could be part of the single rotating member 2 of the pump instead of the casing 1.

It should also be appreciated that other bearing types, for example 'v' bearings, could be utilised in the pump according to the invention instead of the ball and cup bearings shown in the illustrated embodiments of the invention described herein.

A clearance between the impeller shroud 17 and the casing 1 allows a secondary blood flow path 27 between the two parts that washes over the downstream bearing 23. The surfaces of the impeller shroud 17, the casing 1 and the downstream bearing 23 provide a smooth continuous face (see FIG. 4) over which the blood is caused to flow. The pathway is with minimal discontinuity so as to provide for smooth, unhindered flow that is free from areas that could undesirably cause flow statis and consequently thrombus.

With reference to FIG. 4, the area of the downstream bearing 23 that is most likely to be source of a thrombus is the circumferential transition 26 between the rotational bearing ball 24 and the stationary bearing cup 25. Therefore this circumferential transition 26 is directly exposed the secondary blood flow 27 such that the proteinous and cellular components of the blood responsible for thrombus formation are prevented from aggregating in this region.

An entrance 28 to the secondary flow path is defined between the top of the impeller shroud 17 and the casing 1, whilst openings 29 in the single rotating member 2 allow blood from the secondary flow path 27 to rejoin the primary flow path 6. The openings 29 may be created by way of gaps between a series of webs 30 that connect the impeller 11 to the motor rotor 18, both impeller and motor rotor being parts of the single rotating member 2.

The pump is to be attached to the heart by a sewing ring 31 which would typically be attached to the outside of the apex of the ventricle 7 by means of sutures, a tissue compatible adhesive, a combination of the two or another suitable attachment method. A sealing felt (not shown) may be trapped between the sewing ring 31 and the apex 7 to form a blood tight seal around the emergence of the inflow cannula 13 from the apex 7.

Electrical power is provided to the pump by an electrical cable 32. The electrical cable 32 can either be routed percutaneously to an external console and power supply or to an implanted inductive coil for trans-cutaneous power transfer.

Figure 5:
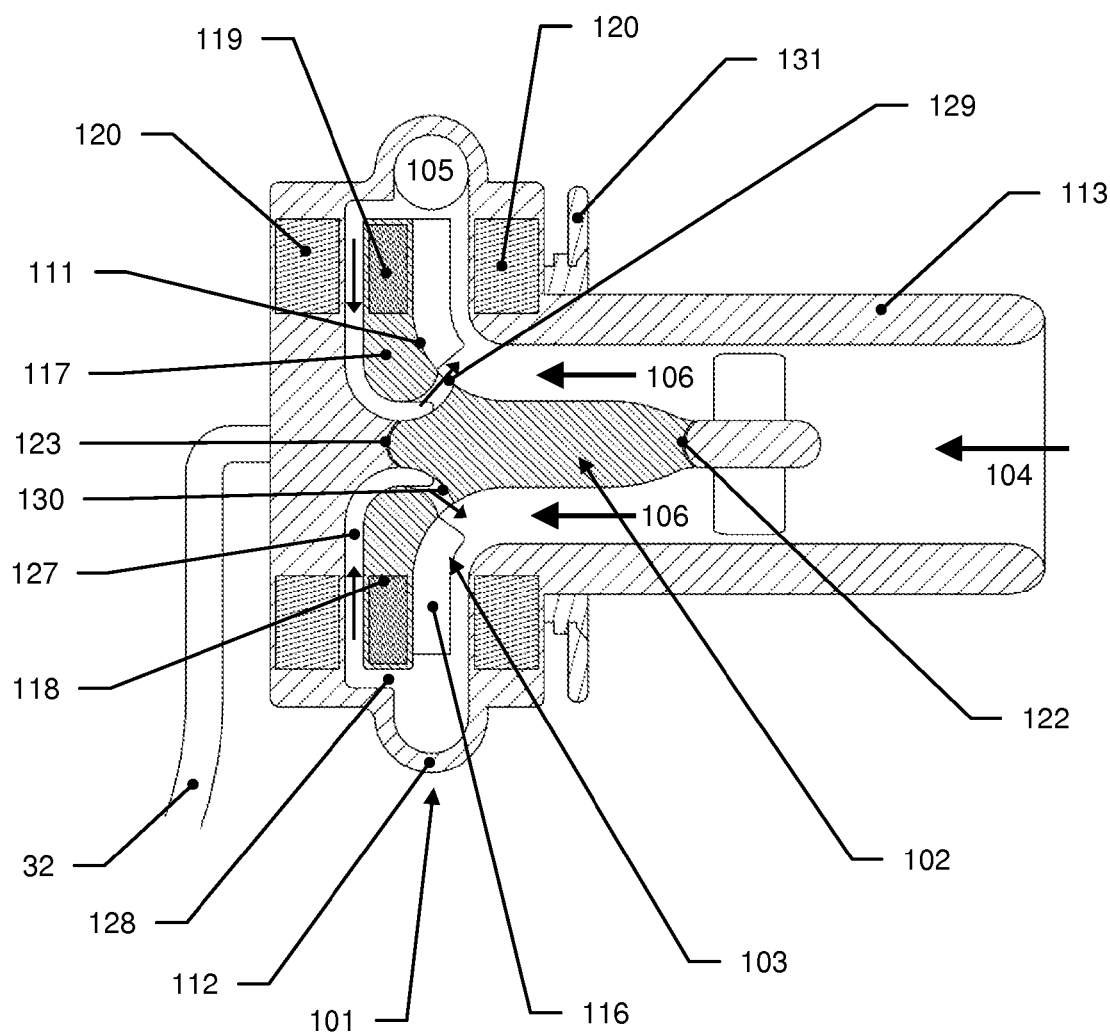
FIG. 5 is a full sectional view of a second embodiment of the pump according to the invention.

With reference to FIG. 5, a second embodiment of a pump according to the invention is shown. The second embodiment primarily differs from the first because the pump uses an axial flux gap motor rather than the radial flux gap motor of the first embodiment. This results in a pump that has a larger pumping chamber 103 outside of the heart but that has a smaller inflow cannula 113.

The layout of the resultant pump is similar that of the first embodiment therefore will be described primarily by way of its differences compared to the first embodiment.

In FIG. 5 there is shown a second embodiment of a cardiac pump, comprising an outer casing 101 and a rotating member 102. Defined by the outer casing 101 and the rotating member 102 is a pumping chamber 103, an inlet 104 for blood, and an outlet 105 for blood. A primary blood flow path 106 is created between the inlet 104 and the outlet 105.

As with the first embodiment, the pumping chamber 103 in use would resides outside of the heart on the apex of the ventricle 7 with its outlet 105 connected to an outflow cannula which is in turn grafted to the descending aorta. The pumping chamber 103 includes an impeller 111 that is an integral part of the rotating member 102. The impeller 111 comprises a series of impeller blades 116 that are connected by a shroud 117. The impeller 111 is is surrounded by a volute 112 which aids the conversion of kinetic energy to pressure energy thus improving efficiency.

As with the previous embodiment, the positioning of the pumping chamber 103 in this second embodiment outside of the heart allows it to be significantly larger than would be possible if it were implanted into the heart, enabling both the impeller 111 and volute 112 to be of an optimised design to the benefit of both pumping capacity and efficiency.

In contrast to the first embodiment the electric motor in the second embodiment is integrated into the pumping chamber 103 and the adjacent casing 101, instead of the motor being integrated into the inflow cannula 113. The permanent magnets 119 of the motor rotor 118 are incorporated into the impeller shroud 117. Two sets of motor coils 120 are positioned in the outer casing 101 such that they are generally axially aligned with the permanent magnets 119 in the motor rotor 118 to allow interaction of the magnetic fluxes. Two sets of motor coils 120 are shown in the second embodiment to balance the axial forces generated in the motor but the motor would function with coils 120 on only one side of the motor rotor 118.

As with the previous embodiment, an inflow cannula 113 extends from the pumping chamber 103, through the wall of the ventricle 114 into the chamber of the ventricle 15, so that the inlet for blood 104 is completely within the chamber of the ventricle (FIG. 1). However, the axial flux gap motor of the second embodiment leads to a larger pumping chamber 103 outside the heart than with the radial flux gap motor of the first embodiment, but it provides for a smaller inflow cannula and thus requires a smaller core to be made into a ventricle of a human heart for implantation.

In other respects the pump of the second embodiment is similar to that of the first.

The single rotating member 102 is rotationally suspended relative to the outer casing 101 by an upstream bearing 122 and a downstream bearing 123, both bearing 122 and bearing 123 being in the form of respective ball and cup members.

A clearance between the impeller shroud 117 and the casing 101 allows a secondary blood flow 127 between the two parts that washes over the downstream bearing 123.

The surfaces of the impeller shroud 117, the casing 101 and the downstream bearing 123 provide a smooth continuous face over which the blood is caused to flow. The pathway is with minimal discontinuity so as to provide for smooth, unhindered flow that is free from areas that could cause deleterious flow statis and consequently thrombus.

An entrance 128 to the secondary flow path is defined between the top of the impeller shroud 117 and the casing 101, whilst openings 129 in the single rotating member 102 allow blood from the secondary flow 127 to rejoin the primary flow path 106. The openings 129 may be created by way of gaps between a series of webs 130 that connect the impeller 111 to the remainder of the single rotating member 102.

The pump is again attached to the heart by a sewing ring 131 (which would typically be attached to the outside of the apex of the ventricle) by means of sutures, a tissue compatible adhesive, a combination of the two or another suitable attachment method. A sealing felt (not shown) may be trapped between the sewing ring 131 and the apex to form a blood tight seal around the emergence of the inflow cannula 113 from the apex.

Electrical power is provided to the pump by an electrical cable 32. The electrical cable 32 can either be routed percutaneously to an external console and power supply or to an implanted inductive coil for trans-cutaneous power transfer.

The invention claimed is:

1. A cardiac pump suitable for implantation into a ventricle of a human heart, the pump comprising:
   a) a housing comprising an inlet for blood, an outlet for blood and a primary blood flow path which extends between the inlet and the outlet;
   b) a rotatable pump member disposed within the housing for causing blood to flow along the primary flow path from the inlet to the outlet, the pump member being rotatably coupled to the housing about an upstream bearing and a downstream bearing, the pump member comprising an impeller which includes an impeller shroud defining a secondary flow path between the pump member and the housing, the secondary flow path comprising an entrance and an exit;
   the entrance and exit being in fluid communication with the primary flow path, with the exit upstream in the primary flow path relative to the entrance, such that blood flow along the primary flow path results in reduction of pressure at the exit relative to that at the entrance and flow of blood along said secondary flow path,
   wherein the downstream bearing comprises a rotational bearing member and a stationary bearing seat for said bearing member, there being a circumferential transition between the bearing seat and the bearing member, the pump having smooth continuous contours in the surfaces of the rotatable pump member and of the housing adjacent said circumferential transition, said circumferential transition being disposed in said secondary flow path and arranged to be washed by continual flow of blood passing along said secondary flow path between the pump member and the housing.

2. A cardiac pump according to claim 1, wherein the exit includes a plurality of openings permitting blood to return to the primary flow path.

3. A cardiac pump according to claim 1, where the exit is arranged to direct blood exiting the secondary flow path into the primary blood flow path in the direction of blood flow along the primary blood flow path adjacent said exit.

4. A cardiac pump according to claim 1, wherein the outlet is disposed downstream of the impeller shroud, such that blood flows through the shroud to the entrance.

5. A cardiac pump according to claim 1, wherein the housing comprises a cannula section and a pump section including a pumping chamber, the inlet being disposed on the cannula section and the outlet being disposed on the pump chamber.

6. A cardiac pump according to claim 5, in which the cannula section is arranged to extend from an internal part of the ventricle to straddle the wall of the ventricle.

7. A cardiac pump according to claim 1, further comprising a rotor and a stator including motor coils for driving the impeller.

8. A cardiac pump according to claim 1, wherein one of the rotational bearing member and the stationary bearing seat is in the form of a cup, and the other of the rotational bearing member and the stationary bearing seat is in the form of a ball seated in the cup.

9. A cardiac pump suitable for implantation into a ventricle of a human heart, the pump comprising:
   a) a housing comprising an inlet for blood, an outlet for blood and a primary blood flow path which extends between the inlet and the outlet;
   b) a rotatable pump member disposed within the housing for causing blood to flow along the primary flow path from the inlet to the outlet, the pump member being rotatably coupled to the housing about an upstream bearing and a downstream bearing, the pump member comprising an impeller which includes an impeller shroud defining a secondary flow path between the pump member and the housing, the secondary flow path comprising an entrance and an exit;
   the entrance and exit being in fluid communication with the primary flow path, with the exit upstream in the primary flow path relative to the entrance, such that blood flow along the primary flow path results in reduction of pressure at the exit relative to that at the entrance and flow of blood along said secondary flow path,
   wherein the downstream bearing comprises a ball and cup bearing having a rotational bearing member and a stationary bearing seat for said bearing member, there being a smooth, continuous circumferential transition between the bearing seat and the bearing member, said circumferential transition being disposed in said secondary flow path and arranged to be washed by blood passing along said secondary flow path.

* * * * *